(12) United States Patent
Harris

(10) Patent No.: US 9,956,093 B1
(45) Date of Patent: May 1, 2018

(54) PROSTHETIC LIMB COVER

(71) Applicant: Warren Harris, Short Hills, NJ (US)

(72) Inventor: Warren Harris, Short Hills, NJ (US)

(*) Notice: Subject to any disclaimer, the term of this patent is extended or adjusted under 35 U.S.C. 154(b) by 0 days. days.

(21) Appl. No.: 15/475,749

(22) Filed: Mar. 31, 2017

(51) Int. Cl.
*A61F 2/60* (2006.01)
*A61F 2/50* (2006.01)
*A61F 2/78* (2006.01)

(52) U.S. Cl.
CPC .................. *A61F 2/60* (2013.01); *A61F 2/78* (2013.01); *A61F 2002/5001* (2013.01); *A61F 2002/5083* (2013.01); *A61F 2002/607* (2013.01); *A61F 2002/7875* (2013.01)

(58) Field of Classification Search
CPC ........ A61F 2/60; A61F 2/78; A61F 2002/601; A61F 2002/607; A61F 2002/5001
See application file for complete search history.

(56) References Cited

U.S. PATENT DOCUMENTS

| | | | | |
|---|---|---|---|---|
| 2,391,537 A * | 12/1945 | Anderson | .............. | A61B 17/66 606/59 |
| 5,880,964 A * | 3/1999 | Schall | .................. | A61F 2/5046 623/27 |
| 7,999,090 B2 * | 8/2011 | Tsukahara | .............. | A61K 31/00 435/254.1 |
| 8,672,865 B2 * | 3/2014 | Franke | .................. | A61F 5/0111 36/117.5 |
| 2004/0158332 A1 * | 8/2004 | Carstens | .................. | A61F 2/78 623/27 |
| 2012/0041567 A1 * | 2/2012 | Cornell | .................... | A61F 2/80 623/33 |

* cited by examiner

*Primary Examiner* — Bruce E Snow
*Assistant Examiner* — Melissa Hoban
(74) *Attorney, Agent, or Firm* — Mitchell J. Mehlman, Esq.

(57) ABSTRACT

Prosthetic limb covers and systems comprising a front shell and a back shell having self-aligning and self-closing features are provided. A prosthetic capture bracket is configured to capture the structural component of a prosthetic device to internally secure the shells to a prosthetic limb.

11 Claims, 5 Drawing Sheets

PROSTHETIC LIMB COVER

BACKGROUND OF THE INVENTION

In medicine, a prosthesis (from Ancient Greek prosthesis, "addition, application, attachment") is an artificial device that replaces a missing body part, which may be lost through trauma, disease, or congenital conditions.

Limb prostheses include both upper- and lower-extremity prostheses. Upper-extremity prostheses are used at varying levels of amputation: forequarter, shoulder disarticulation, transhumeral prosthesis, elbow disarticulation, transradial prosthesis, wrist disarticulation, full hand, partial hand, finger, partial finger.

Lower-extremity prostheses provide replacements at varying levels of amputation. These include hip disarticulation, transfemoral prosthesis, knee disarticulation, transtibial prosthesis, Syme's amputation, foot, partial foot, and toe. The two main subcategories of lower extremity prosthetic devices are trans-tibial (any amputation transecting the tibia bone or a congenital anomaly resulting in a tibial deficiency) and trans-femoral (any amputation transecting the femur bone or a congenital anomaly resulting in a femoral deficiency).

A transfemoral prosthesis is an artificial limb that replaces a leg missing above the knee. Transfemoral amputees can have a very difficult time regaining normal movement. In general, a transfemoral amputee must use approximately 80% more energy to walk than a person with two whole legs. This is due to the complexities in movement associated with the knee. In newer and more improved designs, hydraulics, carbon fiber, mechanical linkages, motors, computer microprocessors, and innovative combinations of these technologies are employed to give more control to the user. In the prosthetic industry, a trans-femoral prosthetic leg is often referred to as an "AK" or above the knee prosthesis.

A transtibial prosthesis is an artificial limb that replaces a leg missing below the knee. A transtibial amputee is usually able to regain normal movement more readily than someone with a transfemoral amputation, due in large part to retaining the knee, which allows for easier movement. Lower extremity prosthetics describes artificially replaced limbs located at the hip level or lower. In the prosthetic industry, a trans-tibial prosthetic leg is often referred to as a "BK" or below the knee prosthesis.

Over the years, there have been advancements in artificial limbs. New plastics and other materials, such as carbon fiber, have allowed artificial limbs to be stronger and lighter, limiting the amount of extra energy necessary to operate the limb. This is especially important for trans-femoral amputees. Additional materials have allowed some artificial limbs to look much more realistic, which is important to transradial and transhumeral amputees because they are more likely to have the artificial limb exposed.

In addition to new materials, the use of electronics has become very common in artificial limbs.

Myoelectric limbs, which control the limbs by converting muscle movements to electrical signals, have become much more common than cable operated limbs. Myoelectric signals are picked up by electrodes, the signal gets integrated and once it exceeds a certain threshold, the prosthetic limb control signal is triggered which is why inherently, all myoelectric controls lag. Conversely, cable control is immediate and physical, and through that offers a certain degree of direct force feedback that myoelectric control does not.

Computers are also used extensively in the manufacturing of limbs. Computer Aided Design and Computer Aided Manufacturing are often used to assist in the design and manufacture of artificial limbs.

Most modern artificial limbs are attached to the stump of the amputee by belts and cuffs or by suction. The stump either directly fits into a socket on the prosthetic, or-more commonly today-a liner is used that then is fixed to the socket either by vacuum (suction sockets) or a pin lock. Liners are soft and by that, they can create a far better suction fit than hard sockets.

Silicone liners can be obtained in standard sizes, mostly with a circular (round) cross section, but for any other stump shape, custom liners can be made. The socket is custom made to fit the residual limb and to distribute the forces of the artificial limb across the area of the stump (rather than just one small spot), which helps reduce wear on the stump. The custom socket is created by taking a plaster cast of the stump or, more commonly today, of the liner worn over the stump, and then making a mold from the plaster cast.

Newer methods include laser guided measuring which can be input directly to a computer allowing for a more sophisticated design.

Cosmetic prosthesis has long been used to disguise injuries and disfigurements. With advances in modern technology, cosmesis, the creation of lifelike limbs made from silicone or PVC has been made possible. Such prosthetics, including artificial hands, can now be designed to simulate the appearance of real hands, complete with freckles, veins, hair, fingerprints and even tattoos.

Custom-made cosmeses are generally more expensive (costing thousands of U.S. dollars, depending on the level of detail), while standard cosmeses come premade in a variety of sizes, although they are often not as realistic as their custom-made counterparts. One option is the custom-made silicone cover, which can be made to match a person's skin tone but not details such as freckles or wrinkles.

Cosmeses are typically attached to the body in any number of ways, using an adhesive, suction, form-fitting, stretchable skin, or a skin sleeve. These devices can be difficult to use, time consuming, and unwieldly.

It is desirable for prosthetic users to utilize some type of prosthetic cover to hide the prosthetic mechanism and provide a smooth limb like surface for supporting clothing. Covers also provide the aesthetic look and feel of a natural limb. The cover allows the user to look and feel like a "normal" person which can have the effect of boosting the user's self-confidence and self-esteem.

Existing prosthesis covers can be bulky and cumbersome. Some covers require the use of screws, buckles, straps, or tools to install or uninstall the covers on a prosthesis.

Some prosthetic covers require complex or tedious fitting operations to ensure the cover fits the prosthesis, such as a lower leg. While still other designs require custom fitting for each user, which can be very costly and time consuming.

For example, U.S. Pat. No. 5,593,453 to Alhert, discloses prosthesis cover formed of waterproof sheet material having leg and foot portions, the foot portion having sole, toe and heel portions and side marginal edges between the toe and sole on both sides of the cover, an antiskid surface covering the foot portion, an open top end, the leg portion having a frusto-conical top segment for engagement with the prosthesis at the top end of the cover, finger loops positioned behind the heel and on opposite sides of the leg portion just below the open top, the leg and foot portions having contours and shape closely conforming to the shape of the prosthesis being covered, and a plurality of inwardly directed ribs being formed on the inner surface of the leg portion of the cover, the plurality of ribs being spaced apart from each other with each rib extending concentrically of the leg portion, the plurality of ribs extending along said inner surface from just above an ankle portion throughout the height of the leg portion to just below the top segment, so that the plurality of ribs spaces the inner cover surface from the prosthesis thereby to reduce frictional engagement when the cover is being applied by sliding over the prosthesis, and so that when the cover is in place the ribs engage the prosthesis and prevent the cover from slipping down along the prosthesis during use.

Thus, it is desirable for a prosthetic cover to include features for easily adjusting to a range of user sizes or lengths while being able to be removably installed or uninstalled quickly and efficiently without the use of screws, buckles, straps, or tools and the like.

The present invention provides novel devices, systems, and methods for improving the ease of use and flexibility of fitting, installing, and uninstalling, prosthetic covers and cover systems.

SUMMARY OF THE INVENTION

In one aspect of the invention an apparatus includes a front shell. The front shell can have a support bracket including a rod and a boss. A back shell has a cradle including a recess, a latch including an aperture for engaging the boss, and a rib having at least one aperture for attaching a prosthetic limb capture bracket. A prosthetic capture bracket includes a rear portion, a front portion, and a hinge. The rear portion has a first aperture for attaching the rear portion to the rib and a second aperture. The front portion has locking means for securing the front portion to the rear portion using the second aperture. A hinge attaches the front and rear portions. The rear portion can be attached to the rib using a fastener such as a screw and the capture bracket can engage a prosthetic device thereby forming a secure cover.

In one embodiment of this aspect, the rod is substantially cylindrical.

In some embodiments of this aspect, the recess is substantially cylindrical.

In certain embodiments, the latch is magnetic and said boss includes a magnet.

In some embodiments of this aspect, the locking means is a locking pin.

In certain embodiments, the prosthetic capture bracket is substantially cylindrical.

In a particular embodiment of this aspect, the front shell and the back shell are configured to be limb shaped.

In another embodiment of the present invention, the limb is a lower leg.

In some embodiments of this aspect, the apparatus can further a prosthetic limb, the limb being removably attached by the capture bracket.

In another non-limiting aspect of the present invention, a limb cover system includes a prosthetic limb. A front shell includes a support bracket having a rod. The front shell includes a boss. A back shell includes a cradle having a recess for engaging the rod, a latch having an aperture for engaging the boss, and a rib having at least one aperture. A prosthetic capture bracket includes a rear portion having a first aperture for attaching the rear portion to the rib using a fastener, and a second aperture for securing the bracket in a closed position. A front portion has a locking means for securing the front portion to the rear portion using the second aperture and a fastener. A hinge attaches the front and rear portions. The rear portion can be attached to the rib using a fastener. The capture bracket can removably engage the prosthetic limb thereby forming a removable cover system.

In some embodiments, the rod is substantially cylindrical.

In certain embodiments, the recess is substantially cylindrical.

In several embodiments, the latch is magnetic and said boss includes a magnet.

In certain embodiments of this aspect, the locking means is a locking pin.

In some embodiments of this aspect, the prosthetic capture bracket is substantially cylindrical.

In certain embodiments, the front shell and the back shell are configured to be limb shaped.

In other embodiments, the limb is a lower leg.

In one embodiment of the instant invention, the prosthetic limb is removably attached by the capture bracket.

DETAILED DESCRIPTION

Figure 1:
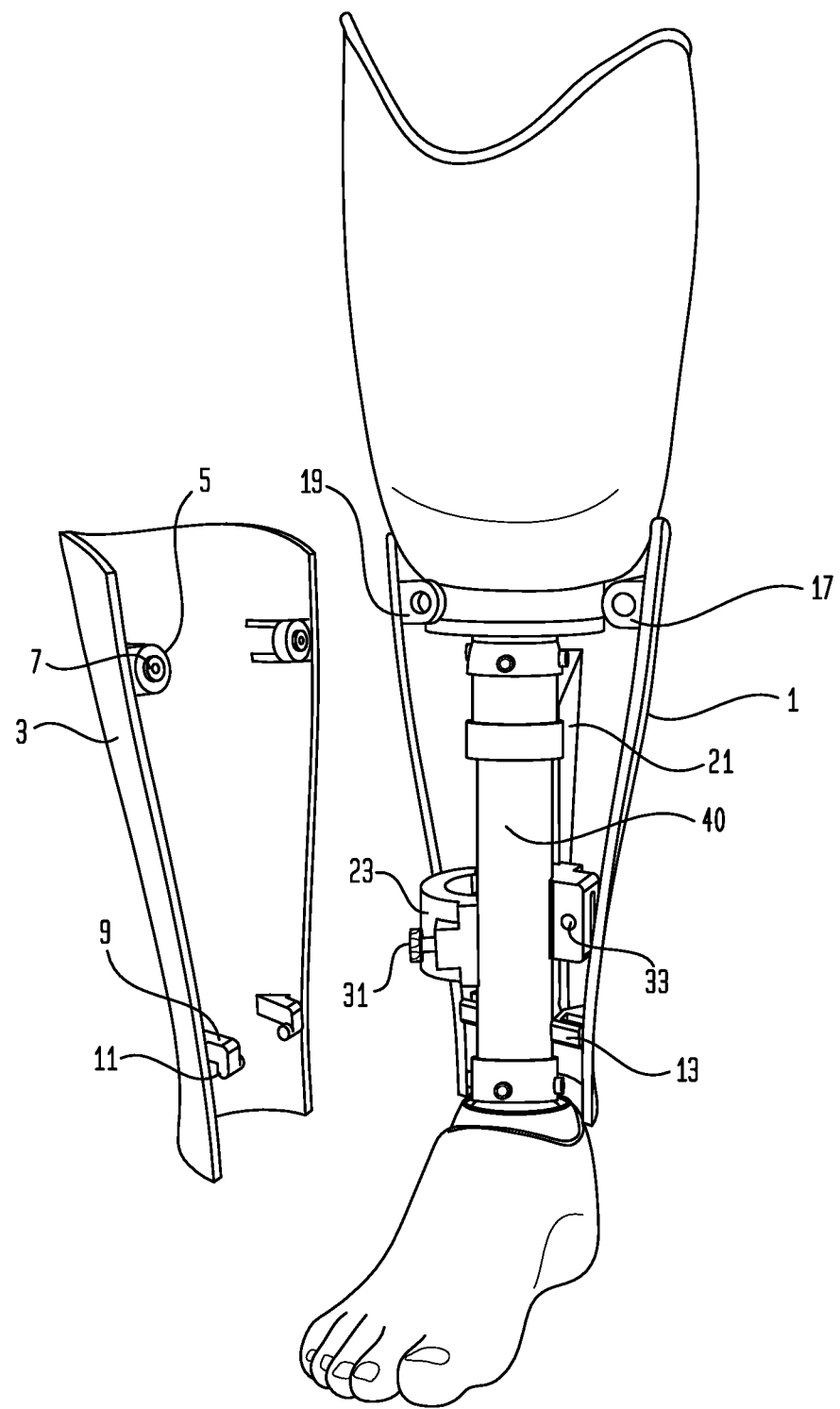
FIG. 1 is an isometric view of a prosthetic limb cover partially installed on a prosthetic leg according to one embodiment of the present invention.

Some of the components of a non-limiting embodiment of the invention as described below may include the following elements: back shell 1, front shell 3, boss 5, magnet 7, support bracket 9, rod 11, cradle 13, cylindrical support 15, latch 17, aperture 19, rib 21, aperture 22, capture bracket 23, rear bracket 25, front bracket 27, hinge 29, locking pin 31, aperture 33, fastener 35, and prosthesis 40.

Figure 2:
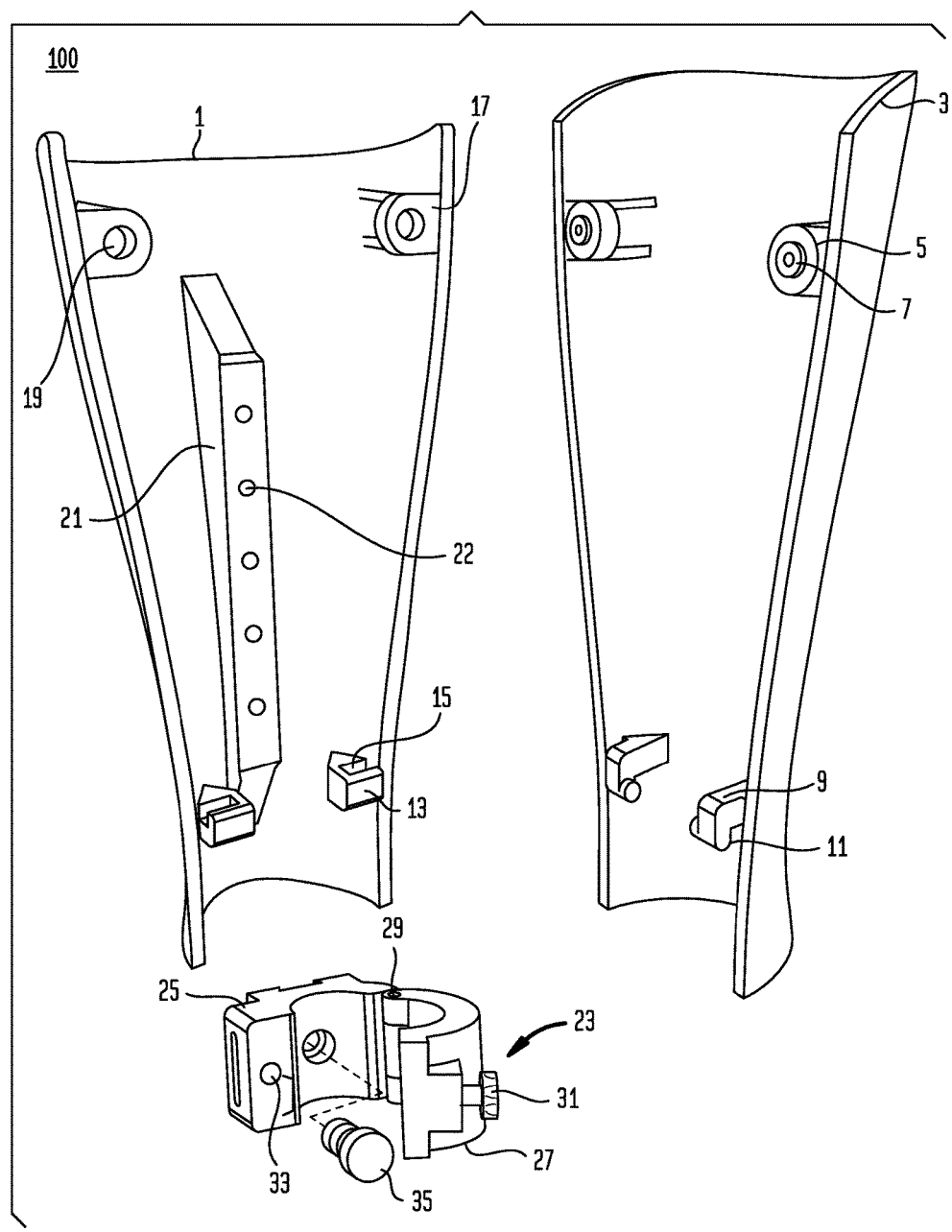
FIG. 2 is an isometric view depicting of some of the elements included in the device of FIG. 1.
Figure 3:
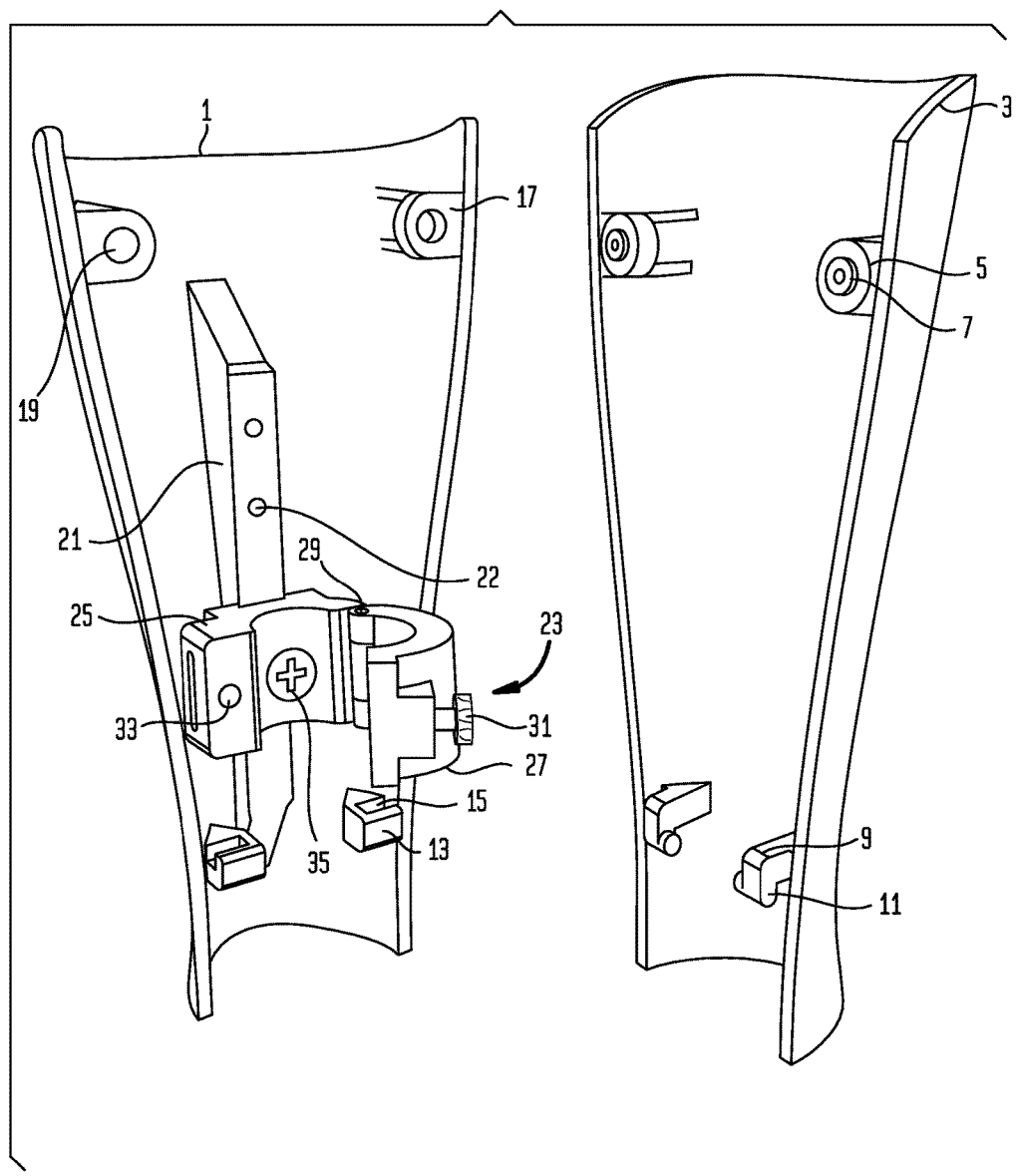
FIG. 3 is an isometric view of some of the elements included in the device of FIG. 1.
Figure 4:
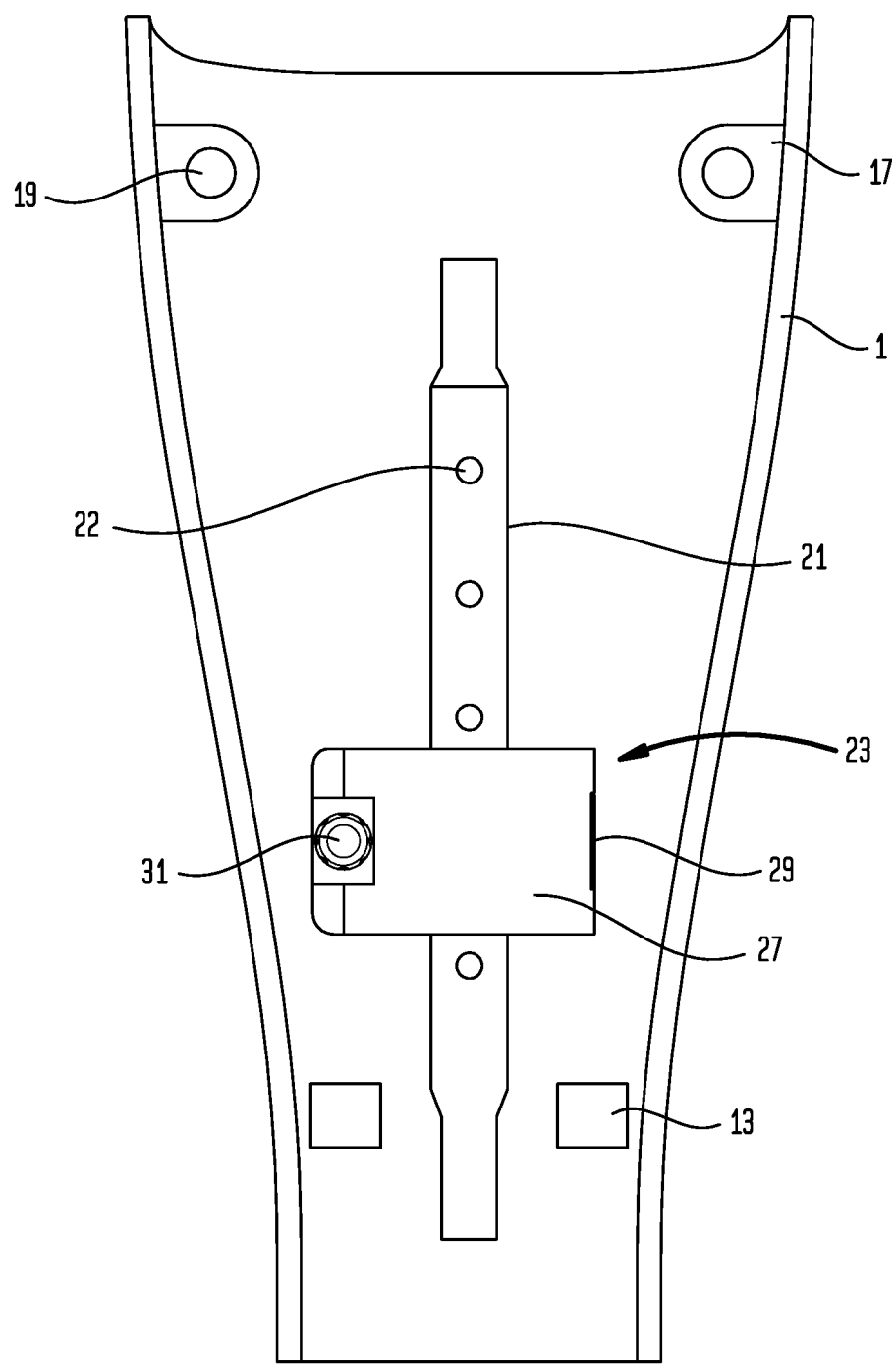
FIG. 4 is a plan view of some of the elements included in the device of FIG. 1.
Figure 5:
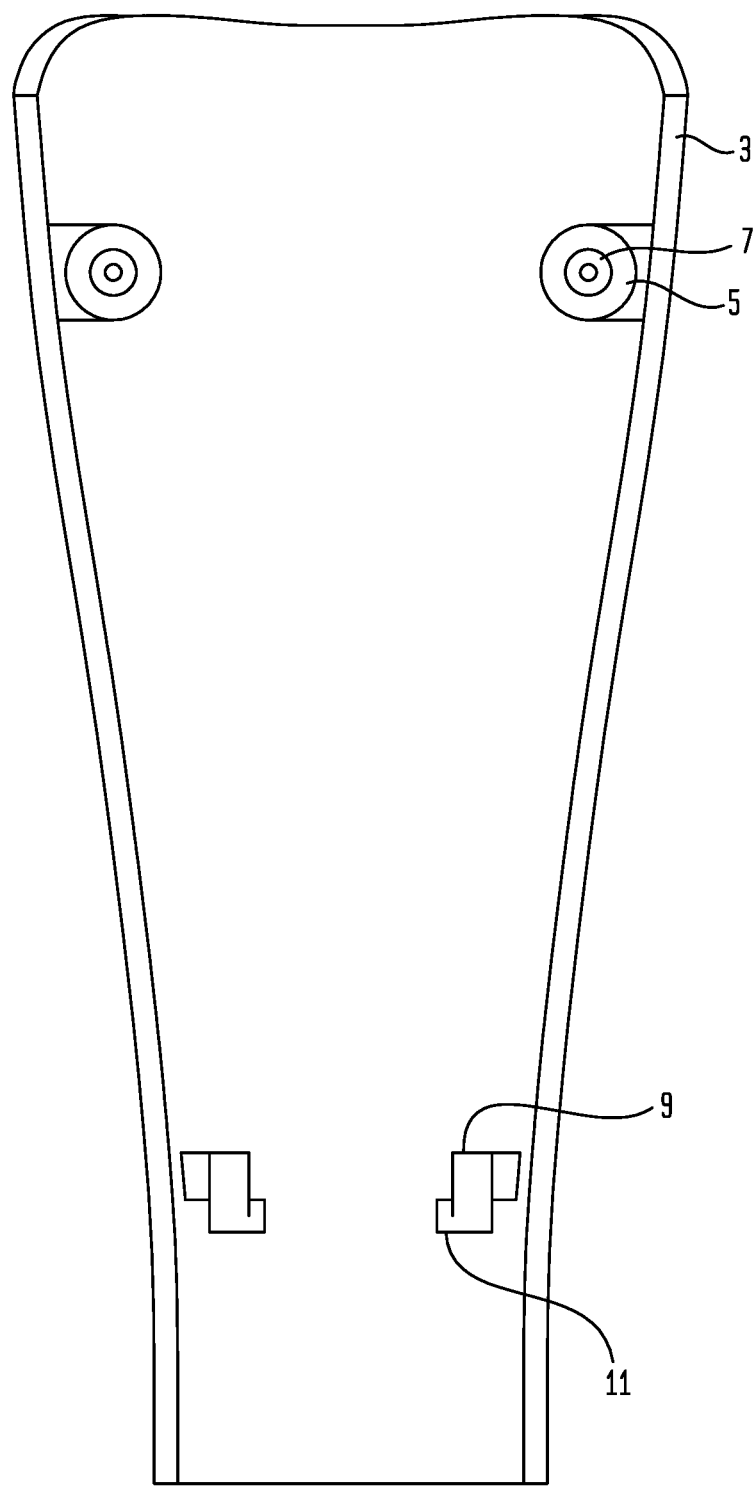
FIG. 5 is a plan view of some of the elements included in the device of FIG. 1.

In one non-limiting embodiment of the present invention as shown in FIGS. 1-5, device 100 includes back shell 1. Back shell 1 includes rib 21. Rib 21 acts as a structural member for attachment of prosthetic capture bracket 23 to a prosthetic limb 40. Rib 21 includes apertures 22, for mounting bracket 23 at a plurality of lengths along the rib. This feature allows for ease and flexibility of adjustment to a wide range of prosthetic devices.

Bracket 23 includes a rear portion 25, a front portion 27 and a hinge 29 connecting the front and rear portions. In this embodiment, the bracket is cylindrically shaped in order to clamp on to and retain a cylindrically shaped prosthesis. Other geometries are contemplated.

Rear portion 27 includes aperture 33 which acts as a locking feature. Front portion 27 includes a pin assembly 31 that can be engaged with aperture 33 to lock the bracket in a closed position. The pin 31 can be a locking type pin, such as for example, a cotterless hitch pin. Locking pin assemblies known to persons of ordinary skill in the mechanical arts are contemplated. Further, any known means of easily securing the bracket to grasp the prosthesis such as screws, pins, quick release devices, latches, locks, and the like are contemplated to be within the scope of the invention. The bracket can be opened and closed easily by a user while allow the user to securely fasten the bracket to a prosthetic device 40 which fits within snugly between the front and rear portions of the bracket.

In this embodiment, back shell 1 includes cradles 13 having cylindrically shaped recesses 15. Front shell 3 includes support brackets 9 having cylindrically shaped rods 11 attached thereto. The rods are configured to engage and rest within recesses 15. Back shell 1 also includes latches 17 having apertures 19. Latches 17 can include a magnetic material.

In use, after the back shell 1 is mounted to a prosthetic device via bracket 23. The rear portion 25 of the bracket 23 includes aperture 29 for mounting the bracket to rib 21 using one of apertures 22 (for height adjustment) and a faster 35, such as a thumb screw, threaded fastener, quick release pin assembly or the like. The front shell can now be mounted such that the rods engage the cradles for proper alignment and easy rotation into position for closing the assembly as discussed below.

Front shell 3 includes bosses 5, having magnets 7 mounted thereto. Once the cradle and rods are engaged, the shells can easily be aligned such that the bosses 5 and latches 17 align in close proximity. The magnets 7 are attracted to latches 17 thereby forming a secure closure adhering the front shell to the back shell. The magnetic force is strong enough to form a secure closure. The shells can be separated using sufficient force thereby forming a prosthetic cover 100 that can be adjusted via the position of the bracket 23 on rib, and easily closed via by engaging the rods and cradles (bottom) and the magnets and latches (10).

It is important to recognize that the cradles and rods produce a self-aligning cover assembly. This feature coupled with the magnetic closure, which produces a self-closing assembly, will increase the users ease of use and decrease the time necessary to attach or detach the cover from a prosthetic limb.

By reversing the process, the device can easily and conveniently be removed from a user's prosthetic limb. For example, the front shell can be disengaged by application of force to separate the magnetic latches. Next, the shell can be rotated such that the rods disengaged from the cradles.

Next, the pin can be disengaged from the aperture such that the front portion of the capture bracket can be rotated on the hinge. This allows the user to remove the back shell from the user's prosthetic by removing the thumb screw. The front and rear shells may now be stored before the next use is desired.

It is contemplated that any size of capture bracket can be used to capture virtually any size of prosthetic limb. For example, typical sizes for a lower limb are 1 inch and 1.5 inch diameters. The bracket and assembly contemplated could be adapted to as smaller assembly, such as an arm, foot, finger or toe proportionally.

Numerous manufacturing methods are contemplated. In particular, 3-D printing technology can be easily adapted to rapidly and efficiently produce components having integral features, such as bosses or rods.

Although the invention herein has been described with reference to particular embodiments, it is to be understood that these embodiments are merely illustrative embodiments and that other arrangements may be devised without departing from the spirit and scope of the present invention as defined by the disclosure herein.

What is claimed is:

1. An apparatus comprising:
    (a) a front shell, said front shell including two internal support brackets, each of said brackets being connected to a portion of said front shell and having a substantially cylindrical rod protruding therefrom, said front shell including two internal bosses, each of said bosses having a magnet connected thereto;
    (b) a back shell, said back shell including two internal cradles, each of said cradles having a substantially cylindrical recess for engaging said rods, two magnetic latches, each latch having an aperture for engaging said bosses, said back shell including an internal vertical rib having at least one aperture, wherein each of said substantially cylindrical rods engages each of said cradles creating a rotational connection between said front shell and said back shell, and allowing engagement of said magnetic latches with said bosses thereby forming a self-aligning removable prosthetic limb cover; and
    (c) a prosthetic capture bracket including a rear portion, a front portion, and a hinge, said rear portion having a fastener for attaching said rear portion to said rib aperture, and an aperture for engaging said front portion, said front portion having a locking pin for securing said front portion to said rear portion using said aperture, and said hinge for rotatably attaching said front and rear portions, wherein said rear portion can be attached to said rib using said fastener and said capture bracket can engage a prosthetic device.

2. The apparatus of claim 1, wherein said locking pin is a quick release locking pin.

3. The apparatus of claim 1, wherein said prosthetic capture bracket is substantially cylindrical.

4. The apparatus of claim 1, wherein said front shell and said back shell are configured to be limb shaped.

5. The apparatus of claim 4, wherein said limb is a lower leg.

6. The apparatus of claim 1, further including a prosthetic limb, said prosthetic limb being removably attached by said capture bracket.

7. An apparatus comprising:
    (a) a prosthetic limb, said limb having a substantially cylindrical portion;
    (b) a front shell, said front shell including two internal support brackets, each of said brackets being connected to a portion of said front shell and having a substantially cylindrical rod protruding therefrom, said front shell including two internal bosses, each of said bosses having a magnet connected thereto;
    (c) a back shell, said back shell including two internal cradles, each having a substantially cylindrical recess for engaging said rods, two magnetic latches, each having an aperture for engaging said bosses and said magnets, and an internal vertical rib having at least one aperture therein, wherein each of said substantially cylindrical rods engages each of said cradles creating a rotational connection between said front shell and said back shell, and allowing engagement of said magnetic latches with said bosses thereby forming a self-aligning removable prosthetic limb cover;
    (d) a prosthetic capture bracket including a rear portion, a front portion, and a hinge, said rear portion having a fastener for attaching said rear portion to said rib aperture, and an aperture for engaging said front portion, said front portion having a locking pin for securing said front portion to said rear portion using said aperture, and said hinge for rotatably attaching said front and rear portions, wherein said rear portion can be attached to said rib using said fastener and said capture bracket can engage said substantially cylindrical portion of said prosthetic device.

8. The apparatus of claim 7, wherein said locking pin is a quick release locking pin.

9. The apparatus of claim 7, wherein said prosthetic capture bracket is substantially cylindrical.

10. The apparatus of claim 7, wherein said front shell and said back shell are configured to be limb shaped.

11. The apparatus of claim 10, wherein said limb is a lower leg.

* * * * *